| United States Patent [19] | [11] 3,994,896 |
|---|---|
| Labovitz et al. | [45] Nov. 30, 1976 |

[54] SULFONATE ESTERS OF NON-4-EN-6-YN-1-OL

[75] Inventors: Jeffery N. Labovitz; Clive A. Henrick, both of Palo Alto, Calif.

[73] Assignee: Zoecon Corporation, Palo Alto, Calif.

[22] Filed: Sept. 12, 1975

[21] Appl. No.: 612,879

Related U.S. Application Data

[62] Division of Ser. No. 526,496, Nov. 25, 1974, Pat. No. 3,954,818.

[52] U.S. Cl. .......................... 260/456 P; 260/456 R; 260/632 Y; 260/654 R; 424/303
[51] Int. Cl.² ........................................ C07C 143/68
[58] Field of Search .................... 260/456 P, 456 R

[56] References Cited
OTHER PUBLICATIONS

Badanyan et al., Chem. Abstract, 81, 90948q (1974).
Porfireva et al., Chem. Abstract, 71, 21616n (1969).
Azatyan et al., Chem. Abstract, 64, 9582(a–c) (1966).

*Primary Examiner*—James O. Thomas, Jr.
*Assistant Examiner*—Nicky Chan
*Attorney, Agent, or Firm*—Donald W. Erickson

[57] ABSTRACT

Steroselective synthesis of the sex pheromone (7E, 9Z)-7,9-dodecadien-1-yl acetate of the grape vine moth *Lobesia botrana* and intermediates therefor.

3 Claims, No Drawings

SULFONATE ESTERS OF NON-4-EN-6-YN-1-OL

This is a division of application Ser. No. 526,496, filed Nov. 25, 1974 now U.S. Pat. No. 3,954,818.

This invention relates to the synthesis of the sex pheromone (7E, 9Z)-7,9-dodecadien-1-yl acetate of the grape vine moth Lobesia botrana (Schiff) and intermediates therefor.

The major sex pheromone of the female grape vine moth has been identified as trans-7, cis-9-dodecadienyl acetate by Roelofs et al, Mitteilunger Der Schweizerischen Entomologoschen Gesellschaft, Band 46, p. 71–73 (1973).

The present invention provides a steroselective synthesis for the preparation of (7E, 9Z)-7,9-dodecadien-1-yl acetate and key intermediates therefor which uses readily available starting material and is economical to practice. The compound can be used as an attractant for monitoring, through selective trapping, the population of Lobesia botrana in a given area. Population counts thus obtained are used in determining the frequency and quantity of spray of insecticide or other insect control agent. The compound can also be used for the direct control of Lobesia botrana by mass trapping or disruption (confusion).

In the preparation of (7E, 9Z)-7,9-dodecadien-1-yl acetate, there is first prepared 1-hepten-4-yn-3-ol (I) as shown below:

$$H_3C-CH_2C \equiv CMg-Br + H(O)C-CH=CH_2 \rightarrow$$
$$H_3C-CH_2-C \equiv C-CH(OH)-CH=CH_2 \quad (I)$$

In the above reaction, 1-butynylmagnesium bromide (prepared from ethylmagnesim bromide and 1-butyne) is reacted with acrolein in approximately 1:1 molar ratio with cooling to below 0° C to readily yield 1-hepten-4-yn-3-ol (I).

This alcohol (I) is then converted to the alcohol (III) of the following formula:

$$H_3C-CH_2-C \equiv C-CH=CH-CH_2-CH_2-CH_2OH \quad (III)$$

In the preferred method for conversion the alcohol (I) is reacted with trimethyl orthoacetate or triethyl orthoacetate in an inert hydrocarbon solvent such as toluene and in the presence of a small amount of a weak acid such as propionic acid as catalyst to yield an ester of formula II (R is methyl or ethyl) wherein the ratio of trans to cis isomers is approximately 80 to 20. See Johnson et al, J. Am Chem. Soc. 92, 742, (1970).

$$CH_3-CH_2-C \equiv C-CH=CH-CH_2-CH_2-COOR \quad (II)$$

The ester (II) is reduced to the alcohol (III) by contacting it with lithium aluminum hydride. In an alternate procedure for preparing the alcohol (III), the alcohol (I) is reacted with ethyl vinyl ether, in the presence of mercuric acetate, followed by heating the vinyl ether at 200° for three hours to yeild an aldehyde of formula II' wherein the ratio of trans to cis isomers is approximately 60 to 40.

$$H_3C-CH_2-C \equiv C-CH=CH_2-CH_2-CHO \quad (II')$$

This general type of reaction is described by Cresson, Compt. Rendus Serie C t. 273 p. 1382 (Nov. 15, 1971) and by Corbier and Cresson, Compt. Rendus Serie C. t. 272. p. 695 (Feb. 15, 1971).

The aldehyde (II') is reduced to the alcohol (III) using sodium borohydride.

The alcohol (III) is converted to an intermediate (IV) and then hydroxypropylated to yield the alcohol (V) as outlined:

$$H_3C-CH_2-C \equiv C-CH=CH-CH_2-CH_2-CH_2-OH \rightarrow \quad (III)$$

$$H_3C-CH_2-C \equiv C-CH=CH-CH_2-CH_2-CH_2-X \rightarrow \quad (IV)$$

$$H_3C_{13CH2}C \equiv C-CH=CH-CH_2-CH_2-CH_2-CH_2-Ch_2-CH_2OH \quad (V)$$

wherein X is p-toluenesulfonyl (tosyl), methaneslfonyl (mesyl) bromo, iodo or chloro.

To convert the alcohol (III) to the intermediate (IV) where X is tosyl or mesyl, the alcohol is treated with tosyl chloride or mesyl chloride. The compound IV where X is bromo is prepared either by combining a tralkylphosphine in carbon tetrabromide and ether with the alcohol (III) or by treating the intermediate IV where X is tosyl or mesyl with sodium bromide in dimethyl formamide.

The hydroxypropylation of the intermediate IV to the alcohol V can be carried out by a variety of methods.

In a convenient and preferred method taught by Eaton et al, J. Org. Chem. 37, 1947 (1972), the organometallic compound $$Li-CH_2CH_2CH_2OCHCH_3$$
$$|$$
$$OCH_2CH_3$$

or $$Mg-CH_2CH_2CH_2OCHCH_3$$
$$|$$
$$OCH_2CH_3$$

is reacted with the intermediate IV where X is bromo at about 0° C in the presence of a copper catalyst such as Li$_2$CuCl$_4$, CuCl, CuI, CuCN, CuCN.LiCl or with an organometallic complex such as R$_2$CULi where R is alkyl, and the like, followed by acid hydrolysis of the protecting group with e.g. trichloroacetic acid to yield the alcohol V, which is readily recrystallized at low temperature to give substantially pure trans alcohol V.

Alternatively, the intermediate IV where X is bromo is treated with magnesium metal to give the corresponding Grignard reagnet which is then reacted with a compound of the formula Br-(CH$_2$)$_3$OY or Br-(CH$_2$)$_2$COOR where Y is a blocking group such as tetrahydropyranyl, 1-ethoxyethyl, tetrahydriofuranyl, trityl, t-butyl, benzyl, trimethylsilyl, t-butyldimethylsilyl, triethylsilyl, tripehenylsilyl, dipehenylmethylsilyl, and the like, and R is alkyl. If the 3-bromocarboxylate is used, the resultant ester group must be reduced with lithium aluminum hydride after the coupling reaction to give the alcohol V.

If desired, the blocking group Y can be removed at this point so that the alcohol (V) can be purified by recrystallization thereby obtaining over 95% of the 7E isomer or the compound $$H_3C-CH_2-C \equiv C-CH-CH-CH_2-CH_2-CH_2-CH_2-CH_2-Ch_2-Ch_2-OY \quad (V')$$

may be used directly in the subsequent conversion to diene outlined below.

The alcohol V is converted to the alcohol

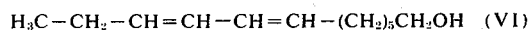

by first protecting the alcohol group with a blocking group such as those listed above or using the protected alcohol (V') prepared above directly.

The selective conversion of the acetylenic bond at C-9 to an olefinic bond is then preferably carried out using disiamylborane following the procedure of Zweifel and Polston, *J. Am. Chem. Soc.* 92, 4068 (1970) or a dialkylaluminum hydride or an aluminum trialkyl, such as diisobutylaluminum hydride, triisobutylaluminum and triethylaluminum, the conversion being carried out at a temperature less than 45° C. See Asigner et al Chem. Ber. 97, 1555–61 (1964) and Wilke and Muller, *Chem. Ber.* 89,444–7 (1956). The protecting troup is then removed. The blocking group is in the alcohol (VI) can be removed under mild conditions using procedures that depend upon the nature of the protecting group but, generally, the mildest possible conditions are desirable to protect the trans, cis stereochemistry. Hydrolyzing agents may be water or dilute aqueous or alcoholic solutions of acids, such as p-toluenesulfonic acid, sulfuric acid, hydrochloric acid, hydrobromic acid, nitric acid, acetic acid, perchloric acid, etc. When the protecting group is a completely organic ether or acetal group, from about 0.2 to about 2.5 moles of acid per mole of ether may be intimately mixed with the ether coupling product in aqueous ethanol or other alcohol or aqueous tetrahydrofuran for from about two to four hours at temperatures ranging from 20° to about 50° C. Under these acidic conditions, it is preferable to employ lower tempertures and larger ratio of acid to water alcohol than to use elevated temperatures and a smaller amount of acid. When the protecting group is a silyl group, such as trimethylsilyl, the protecting group may be removed by merely boiling for several minutes with a small amount of water with sufficient alcohol to give a homogeneous solution as described in J. Am. Chem. Soc.., 74, 3024 (1952). In the absence of acid, elevated temperatures may be used.

The tert-butyldimethylsilyl group can be removed by treatment with about 3 equivalents of tetra-n-butylammonium fluoride in tetrahydrofuran using the method of Corey and Venkateswarlu, *J, Am. Chem. Soc.* 94 6190 (1972).

Alternatively, the alcohol (VI) can be directly obtained by selective hydrogenation of the alcohol (V) using hydrogen gas and Lindlar catalyst at low temperature.

The desired (7E, 9Z)-7,9-dodecadienyl acetate is prepared from the alcohol by any of the conventional acetylation methods known in the art, for example, by reacting with acetic anhydride in the presence of pyridine.

The following examples are provided to illustrate the present invention. All temperatures are in degrees Centigrade. Boiling points are for short path distillation.

EXAMPLE 1

To a solution of 3 M ethylmagnesium bromide in ethyl ether (330 ml.., 1 mole) is added via a gas inlet tube 60 g. (1.1 mole) of 1-butyne. Addition of the gas is carried out over 1.5 hour at such a rate that the ether refluxes gently. Exit gases are trapped at −78° and recirculated through the solution after 60 g. of butyne have been added. The solution of 1-bytynylmagnesium bromide is then cooled to −20° C and there is added dropwise a solution of 70 ml. of acrolein (1.1 mole) in 180 ml. of dry ether at such a rate that the internal temperature never exceeds 0° C. After addition is complete, the mixture is allowed to reach room temperature. The solution is then cooled to 0° and saturated ammonium chloride is cautiously added with vigourous stirring. The ether layer is decanted from the precipitated salts and the salts are washed with ether. The combined organic phase is washed with saturated ammonium chloride, 2 N NaOH and brine successively. The organic phase is dried over sodium sulfate and solvent is removed under reduced pressure. The residual oil (95 g.) is used in the next step without purification.

EXAMPLE 2

Crude 1-hepten-4-yn-3-ol, (95 g.) is mixed with 300 g. of trimethyl orthoacetate and 300 ml. of toluene. There is then added 3 ml. of propionic acid and the mixture is heated until distillation of the methanol-toluene azeotrope begins (b.p. ∼ 85° ). Distillate is collected over a period of six hours and totals approximately 300 ml. During this time the distillation temperature rises from 85° to 100°. The reaction mixture is then concentrated below 70° under reduced pressure and the residue is distilled at 20 mm. The fractions boiling at 122°–130° (20 mm.) and 130°–132° (20 mm.) are collected for a total yield of 76 g. of methyl 4-nonen-6-ynoate. Gas liquid chromatographic analysis indicates the first major fraction (68 g.) to contain about 20% of the cis-4 isomer while the higher boiling fraction contains about 10% of this isomer.

Further purification by fractional distillation or spinning band distillation yields all trans methyl 4-nonen-6-ynoate.

EXAMPLE 3

Methyl non-4-en-6-nyoate (39 g., 0.233 moles) dissolved in 200 ml. of anhydrous tetrahydroufruan is added to a solution of 33.8 ml. of 4.3 M lithium aluminum hydride (0.146 moles) in 100 ml. of tetrahydrofuran. The addition is carried out in such a rate as to maintain a gentle reflux. After addition is complete the reaction is over. The mixture is cooled and 5.5 ml. of water is added cautiously dropwise followed by 5.5 ml. of 20% sodium hydroxide and an additional 10 ml. of water. The granular precipitate was removed by filtration and washed with ether. The combined organic phases are concentrated in vacuo and the residue distilled to give 26.7 g. (83%) of non-4-en-6-yn1-ol b.p. 65° (0.200 mm.). This product is an 80 to 20 mixture of trans and cis isomers.

EXAMPLE 4

To a mixture of p-toluenesulfonyl chloride (22.4 g., 0.12 moles) and 50 ml. of anhydrous pyridine is added 14 g. of non-4-en-6-yn-1-ol (0.107 moles) with ice bath cooling. The mixture is stirred for 1 hour and then is stored at 0° overnight. Ice is added to the mixture which is extracted with several portions of 50:50 ether/hexane. The combined organic phase is washed with 5% HCl, water, saturated sodium bicarbonate and dried over sodium sulfate. Removal of solvent at reduced pressure and subsequent solvent removal at 0.1 mm. for 1 hour gives 1-tosyloxy-non-4-en-6yne (28 g.).

EXAMPLE 5

To a solution of 42.7 g. of 1-tosyloxynon-4-en-6-yne (0.14 moles) in 150 ml. of anhydrous dimethylformamide is added 18.7 g. of sodium bromide (0.16 moles) and the mixture is heated at 75° for 2 hour and then allowed to stir overnight at room temperature. The reaction mixture is then diluted with 200 ml. of ice water and extracted with pentane. The pentane extract is washed with water and dried over sodium sulfate. Evaporation of solvent in vacuo and distillation of the residue oil gave 24.3 g. of 1-bromonon-4-en-6-yne (84% yield) b.p. 52°–55° at 0.15 mm.

EXAMPLE 6

Clean lithium wire containing 1% sodium (980 mg., 0.14 moles) is cut into small pieces and suspended in 30 ml. of anhydrous ether under an argon atmosphere. To the suspension at 0° is added about 200 mg. of 1-bromo-3-[(1-ethoxy)ethoxy] propane which has previously been prepared from 3-brompproan-1-ol and ethyl vinyl ether. After the reaction has begun as detected by a silvery appearance of the lithium, the mixture is cooled to —5° and the remainder of the bromoacetal in 20 ml. of dry ether is added dropwise at —10° to —5° over 35 minutes. The mixture is then stirred for an additional 2 hours. Titration with 1 M sec-butanol in xylene using 1,10-phenanthroline as an indicator showed the final ethereal solution to be 0.56 molar in organo lithium reagent, 3-[(1-ethoxy)-ethoxy]propyllithium.

EXAMPLE 7

To 42 ml. of anhyrous tetrahydrofuran is added 31.8 ml. of 0.56 M lithium reagent (prepared in Example 6) at 0°. There is then added 15 ml. of 1 M $Li_2CuCl_4$ in tetrahydrofuran followed by 3.01 g. (15 mmole) of 1-bromonon -4-en-6The reaction mixture is stirred at 0° to —5° for 15 minutes when an additional 13 ml.of 0.56 M lithium reagent is added. After 40 minutes, the solution still contains active lithium reagent as determined by Gilman test. Saturated ammonium chloride solution is added and the mixture is then extracted with ether. The combined organic layers are washed with saturated ammonium chloride and then brine. The organic phase is dried over magnesium sulfate and the solvent is removed in vacuo. The residual oil (3.7 g.) is taken up in 60 ml. of tetrahyroufran and there is added 40 ml. of water and 300 mg. of trichloroacetic acid. The mixture is heated at 60° for 1 hour during which time the mixture becomes completely homogeneous. The mixture is cooled and extracted with pentane. The pentane extracts are combined and washed with 5% sodium bicarbonate solution and brine, then dried over magnesium sulfate. After removal of the solvent in vacuo there remains 2.35 g. of residual oil which contains 78% of the desired alcohol. One recrystallization of the crude oil from pentane at —35° provided 1.35 g. of (E)dodec-7-en-9-yn-1-ol with a purity of 98.6%.

EXAMPLE 8

To a solution of 15 g. (83 mmole of (E)-dodec-7-en-9-yn-1ol in 100 ml. of methylene chloride containing 9 g. of triethylamine is added dropwise trimethylsilylchloride at such a rate that gentle reflux is observed. The mixture is allowed to stir for 1 hour after addition is complete. methylene chloride solution is then poured into 300 ml. of pentane and filtered. The precipitated salts are washed with pentane and solvent is removed in vacuo. The residue is taken up in 300 ml. of pentane and filtered again. The filtrate is evaporated in vacuo and the residual (E)-1-trimethylsilyloxydodec-7en-9-yne is used in the next stage without additional purification.

To a solution of the trimethylsilyl ether (21 g., 82 mmole) in 100 ml. of anhydrous tetrahydrofuran maintained at 0° is added 195 ml. of disiamlyborane (0.475 M in tetrahydrofuran). The reaction mixture is kept at 0° for 2 hours and then 50 ml. of glacial acetic acid is added. The mixture is heated at 65° for 4 hour, left overnight at room temperature and heated at 65° for one additional hour. After cooling, the 400 ml. of sodium hydroxide followed by cautious addition (at 35°) of 30 ml. of 30% $H_2O_2$. The oxidation is allowed to proceed for 1 hour after addition of the hydrogen peroxide. The organic phase is separated and the aqueous phase is extracted with pentane. The combined organic phase and extracts are washed with 3 N sodium hydroxide and brine. After drying over sodium sulfate and evaportion in vacuo the residual oil is taken up in 200 ml. of methanol and treated with 300 mg. trichloroacetic acid at room temperature for one hour. The alcoholic hydrolysis mixture is treated with saturated sodium bicarbonate and concentrated in vacuo to about ½ volume. Pentane is added and the organic phase is separated. The aqueous phae is extracted with pentane and the combined organic phases are dried over sodium sulfate and evaporated in vacuo. The residual oil is distilled to give 10.03 g. (7E,9Z)-7,9-dodecadien-1-ol, b.p. 85° (0.16 mm.), 67% yield.

EXAMPLE 9

To a solution of 7.5 g. of (7E,9Z)-7,9-dodecadien-1-ol in 12 ml. of freshly distilled pyridine is added 6 ml. of acetic anhydride with water bath cooling in order to maintain the temperature below 30°. The mixture is stored at room temperature overnight and then is poured into 200 ml. of cold saturated sodium bicarbonate solution. The mixture is extracted with pentane and the pentane extracts washed with 1N hydrochloric acid, water and then dried over sodium sulfate.

Evaporation of the solvent in vacuo followed by distillation of the residue provided 8.3 g. (7E,9Z)-7,9-dodecadienyl acetate, b.p. 86.5 (0.2 mm) 99.3% pure.

What we claim is:

1. A compound of the formula:

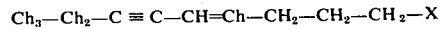

wherein X is p-toluenesulfonyloxy or methanesulfonyloxy.

2. The trans isomer of a compound according to claim 1.

3. The compound, 1-(p-toluenesulfonyloxy)4-nonen-6-yne, according to claim 1.

* * * * *